US012758319B2

(12) United States Patent
Christen et al.

(10) Patent No.: US 12,758,319 B2
(45) Date of Patent: Oct. 13, 2026

(54) TECHNIQUE FOR PROVIDING USER GUIDANCE IN SURGICAL NAVIGATION

(71) Applicant: Stryker European Operations Limited, Carrigtwohill (IE)

(72) Inventors: Alexis Christen, Herzogenbuchsee (CH); Jakob Kemper, Heemstede (NL); Matthias Paulisch, Roggwil (CH); Ulrich Hoffmann, Breisach (DE); Fabian Huegle, March (DE); Lars Metz, Kiel (DE); Ulrich Spaelter, Schoellbronn (DE)

(73) Assignee: Stryker European Operations Limited, Carrigtwohill (IE)

( * ) Notice: Subject to any disclaimer, the term of this patent is extended or adjusted under 35 U.S.C. 154(b) by 334 days.

(21) Appl. No.: 18/072,116

(22) Filed: Nov. 30, 2022

(65) Prior Publication Data

US 2023/0087163 A1 Mar. 23, 2023

Related U.S. Application Data

(63) Continuation of application No. 16/893,883, filed on Jun. 5, 2020, now Pat. No. 11,540,887.

(51) Int. Cl.
*A61B 34/20* (2016.01)
*A61B 34/10* (2016.01)

(52) U.S. Cl.
CPC .............. *A61B 34/20* (2016.02); *A61B 34/10* (2016.02); *A61B 2034/102* (2016.02); (Continued)

(58) Field of Classification Search
CPC ............ A61B 17/1725; A61B 17/1728; A61B 17/808; A61B 2017/564; A61B 2034/102; (Continued)

(56) References Cited

U.S. PATENT DOCUMENTS 8,320,612 B2 11/2012 Knobel et al.
9,901,407 B2 2/2018 Breisacher et al.
(Continued)

FOREIGN PATENT DOCUMENTS

DE 102008023760 A1 12/2009
DE 102009025248 A1 11/2010
(Continued)

OTHER PUBLICATIONS

English language abstract and machine-assisted English translation for DE 10 2008 023 760 extracted from espacenet.com database on Oct. 8, 2020, 6 pages.
(Continued)

*Primary Examiner* — Michael T Rozanski
(74) *Attorney, Agent, or Firm* — Howard & Howard Attorneys PLLC

(57) ABSTRACT

A technique of providing user guidance for surgical navigation is provided. A method implementation of the technique includes obtaining a predetermined spatial relationship between an optical tracking pattern and a through-hole extending through an implant, obtaining image data of the optical tracking pattern acquired by an imaging unit attached to a surgical instrument, obtaining a spatial relationship between the surgical instrument and the imaging unit at a point in time when the image data have been acquired, determining a spatial relationship between the surgical instrument and the through-hole, obtaining a plurality of predefined spatial relationships between the surgical instrument and the through-hole, and triggering simultaneous display of an indication of the plurality of predefined spatial relationships and an indication of the spatial relationship between the surgical instrument and the through-hole.

19 Claims, 5 Drawing Sheets

(52) U.S. Cl.
CPC . *A61B 2034/105* (2016.02); *A61B 2034/2055* (2016.02); *A61B 2034/2065* (2016.02)

(58) Field of Classification Search
CPC ........ A61B 2034/105; A61B 2034/107; A61B 2034/2055; A61B 2034/2057; A61B 2034/2065; A61B 2090/3983; A61B 34/10; A61B 34/20; A61B 34/25
See application file for complete search history.

(56) References Cited

U.S. PATENT DOCUMENTS

| | | | |
|---|---|---|---|
| 9,987,093 | B2 | 6/2018 | Christian et al. |
| 2009/0259230 | A1 | 10/2009 | Khadem et al. |
| 2009/0270928 | A1 | 10/2009 | Stone et al. |
| 2011/0190637 | A1 | 8/2011 | Knobel et al. |
| 2016/0135903 | A1 | 5/2016 | Christian et al. |
| 2018/0132946 | A1 | 5/2018 | Kao et al. |
| 2018/0217734 | A1 | 8/2018 | Koenig et al. |
| 2020/0170802 | A1 | 6/2020 | Casey |
| 2021/0378753 | A1 | 12/2021 | Christen et al. |

FOREIGN PATENT DOCUMENTS

| | | | |
|---|---|---|---|
| DE | 102010041564 | A1 | 3/2012 |
| DE | 102011007512 | A1 | 10/2012 |
| DE | 102011086720 | A1 | 5/2013 |
| DE | 102012209448 | A1 | 12/2013 |
| DE | 102012209450 | A1 | 12/2013 |
| EP | 1527417 | B1 | 9/2011 |
| EP | 1534141 | B1 | 8/2013 |
| EP | 2326276 | B1 | 4/2014 |
| EP | 2377484 | B1 | 8/2015 |
| EP | 2008244 | B1 | 4/2016 |
| EP | 2467080 | B1 | 4/2018 |
| EP | 2723270 | B1 | 1/2019 |
| EP | 3692939 | A1 | 8/2020 |
| KR | 20160101138 | A | 8/2016 |
| WO | 0047103 | A2 | 8/2000 |
| WO | 03043485 | A2 | 5/2003 |
| WO | 2012109760 | A1 | 8/2012 |
| WO | 2015003727 | A1 | 1/2015 |
| WO | 2015148378 | A1 | 10/2015 |
| WO | 2018007091 | A1 | 1/2018 |
| WO | 2019141704 | A1 | 7/2019 |

OTHER PUBLICATIONS

English language abstract and machine-assisted English translation for DE 10 2010 041 564 extracted from espacenet.com database on Oct. 8, 2020, 6 pages.
English language abstract and machine-assisted English translation for DE 10 2011 007 512 extracted from espacenet.com database on Oct. 8, 2020, 7 pages.
English language abstract and machine-assisted English translation for DE 10 2011 086 720 extracted from espacenet.com database on Oct. 8, 2020, 9 pages.
English language abstract and machine-assisted English translation for DE 10 2012 209 448 extracted from espacenet.com database on Oct. 8, 2020, 13 pages.
English language abstract and machine-assisted English translation for DE 10 2012 209 450 extracted from espacenet.com database on Oct. 8, 2020, 10 pages.
English language abstract and machine-assisted English translation for WO 2018/007091 extracted from espacenet.com database on Oct. 8, 2020, 11 pages.
English language abstract for EP 2 326 276 extracted from espacenet.com database on Oct. 8, 2020, 1 page.
English language abstract for EP 2 377 484 extracted from espacenet.com database on Oct. 8, 2020, 2 pages.
Machine-assisted English language abstract and machine-assisted English translation for DE 10 2009 025 248 extracted from espacenet.com database on Oct. 8, 2020, 7 pages.

TECHNIQUE FOR PROVIDING USER GUIDANCE IN SURGICAL NAVIGATION

CROSS-REFERENCE TO RELATED APPLICATIONS

This is a continuation of co-pending U.S. application Ser. No. 16/893,883, filed Jun. 5, 2020, the entire contents of which are hereby incorporated by reference.

TECHNICAL FIELD

The present disclosure generally relates to surgical navigation. In particular, a method of providing user guidance in surgical navigation, a processor, a computer program and a carrier are disclosed.

BACKGROUND

Surgical navigation generally provides a surgeon with information useful for surgery. For example, a pose (i.e., at least one of a position and an orientation) of a surgical instrument (e.g., a chisel, a drill, a trocar, a screwdriver, a pointer or the like) can be visualized relative to patient image data. The patient image data may be two- or three-dimensional image data of a patient acquired using a medical image acquisition technique such as computed tomography or magnetic resonance imaging. A tracking system may be used to track the pose of the surgical instrument relative to a body of the patient by localizing trackers attached to the surgical instrument and the body, respectively.

In some cases, a pose of an implant (e.g., a bone plate, an artificial organ or the like) relative to at least one of the body and the surgical instrument may be of interest to the surgeon. For example, a bone plate may need to be screwed in a desired pose to a bone of a patient, by screwing fixation screws through respective holes in the bone plate. The bone to which the bone plate is to be attached may lie beneath (e.g., critical) anatomical structures of the body of the patient which shall not be injured during surgery. Especially in these cases, minimal-invasive surgery may be advantageous.

In such minimal-invasive surgery, the bone plate may be inserted through a narrow opening in the body of the patient and be positioned on the bone in the desired pose. The bone plate in the desired pose may not be visible to at least one of the surgeon and the tracking system. Thus, for positioning the bone plate relative to the body of the patient, a placement instrument, which may be attached relative to the bone plate in a predetermined spatial relationship, may be tracked by the tracking system. The placement instrument may be used by the surgeon to move the bone plate into the desired pose and may comprise a tracker.

After placement of the bone plate in the desired pose on the bone of the patient's body, fixation screws may need to be screwed through the respective holes in the bone plate to fix the bone plate onto the bone. As mentioned before, the implant, and, consequently, also the holes of the bone plate, may not be visible to at least one of the surgeon and the tracking system after placement of the bone plate in the desired pose. Nevertheless, the pose of the implant relative to the patient's body may still be determined by the tracking system by tracking at least one tracker attached to the placement instrument and at least one tracker attached to the patient's body.

In order to guide the surgeon, information of the relative pose between the surgical instrument and a hole in the bone plate may be advantageous. Providing such information requires determining a relative pose between the surgical instrument and the bone plate.

In some cases, simultaneous visibility of trackers attached to the placement instrument and the surgical instrument may be blocked, for example by an arm of the surgeon. It may therefore be advantageous to ensure a good visibility of these trackers at all times, for example when a screwdriver is being used to screw the fixation screws though the respective holes of the bone plate.

SUMMARY

There is a need for a technique of providing user guidance in surgical navigation that solves one or more of the aforementioned or other problems.

According to a first aspect, a method of providing user guidance for surgical navigation is provided. The method comprises obtaining implant data representative of a spatial relationship between an optical tracking pattern and a through-hole extending through an implant. The method also comprises obtaining image data representative of at least a part of the optical tracking pattern, the image data having been acquired by an imaging unit attached to a surgical instrument, and obtaining instrument data representative of a spatial relationship between the surgical instrument and the imaging unit at a point in time when the image data have been acquired. The method also comprises determining, based on the implant data, the image data and the instrument data, tracking data describing a spatial relationship between the surgical instrument and the through-hole, and obtaining guidance data describing a plurality of predefined spatial relationships between the surgical instrument and the through-hole.

The method further comprises triggering, based on the tracking data and the guidance data, simultaneous display of an indication of the plurality of predefined spatial relationships and an indication of the spatial relationship between the surgical instrument and the through-hole.

The step of obtaining the guidance data may comprise or be followed by a step of determining a border with respect to the through-hole, the border separating a first region in space from a second region in space.

The border may be defined in one spatial dimension (e.g., as a line) or in two spatial dimensions (e.g., as a plane) or in three spatial dimensions (e.g., as at least a part of a surface of a three-dimensional body). That is, the border may be a one-dimensional border (e.g., a continuous straight line), a two-dimensional border (e.g., a closed line such as a ring) or a three-dimensional border (e.g., a closed surface such as a plane or a surface of a three-dimensional body such as a cylinder or a cone).

The border may be determined such that, when the surgical instrument is in any one of the plurality of predefined spatial relationships, it is located (e.g., at least one of positioned and oriented) in the first region and, when it is in another spatial relationship not corresponding to one of the plurality of predefined spatial relationships, it is located in the second region. The border may define more than one predefined spatial relationship. To this end, the border may limit, define, enclose or indicate an extended spatial region or volume within which the predefined spatial relationships are located.

The indication of the plurality of predefined spatial relationships may comprise a visualization of at least a part of the border. The at least a part of the border may lie within a predetermined maximal distance from a center or center axis of the through-hole. The part of the border may lie within a predetermined maximal distance from a center or center axis of the through-hole. As such, the border may define more than one predefined spatial relationship. The border may be visualized as a one-dimensional border (e.g., as an optically continuous straight line), as a two-dimensional border (e.g., as an optionally closed line such as a ring) or as a three-dimensional border (e.g., as an optionally closed surface such as a cylinder or a cone). The visualization of the at least a part of the border may be a one-dimensional visualization such as a straight line, for example an optically continuous straight line. The visualization of the at least a part of the border may be a two-dimensional visualization such as a curved or closed line, for example an optionally closed line (e.g., a ring, an oval, a polygon or the like). The visualization of the at least a part of the border may be a three-dimensional visualization such as a (e.g., two-dimensional projection of a three-dimensional) surface, for example an optionally closed or continuous surface.

The step of triggering simultaneous display may comprise triggering display of a visualization representing a view along an (e.g., the) axis of the surgical instrument, wherein the visualization optionally further visualizes the at least a part of the border and, optionally, a (e.g., the) center axis of the through-hole. Additionally, or in the alternative, the step of triggering simultaneous display may comprise triggering display of a visualization representing a view along a (e.g., the) center axis of the through-hole, the visualization optionally further visualizing the at least a part of the border and, optionally, an (e.g., the) axis of the surgical instrument.

The indication of the plurality of predefined spatial relationships may comprise a different visualization of at least a part of the first region compared to the second region. The indication of the plurality of predefined spatial relationships may comprise a different visualization of at least a part of the second region compared to the first region. At least one of the at least a part of the first region and the at least a part of the second region may lie within a predetermined maximal distance from a center or center axis of the through-hole. At least one of the part of the first region and the part of the second region may lie within a predetermined maximal distance from a center or center axis of the through-hole.

The first region may be (e.g., essentially) rotationally symmetric. The first region may be (e.g., essentially) rotationally symmetric around a (e.g., the) center axis of the through-hole. The first region may be (e.g., essentially) conical. A tip of the first region may lie on a (e.g., the) center or center axis of the through-hole.

The indication of the spatial relationship between the surgical instrument and the through-hole may comprise a visualization of a pose (i.e., at least one of a position and an orientation) of an axis of the surgical instrument. The pose of the axis may be visualized relative to a (e.g., the) center axis of the through-hole. The axis of the surgical instrument may be a longitudinal axis or an axis parallel to an insertion direction of the surgical instrument.

The indication of the spatial relationship between the surgical instrument and the through-hole may comprise a visualization of an offset of a tip of the surgical instrument from a (e.g., the) center or center axis of the through-hole.

The instrument data may describe a predetermined spatial relationship between the surgical instrument and the imaging unit defined by a mechanical interface configured to (e.g., removably) attach the imaging unit relative to the surgical instrument. The mechanical interface may fix the imaging unit on or relative to the surgical instrument, or vice versa.

The method may further comprise simultaneously displaying (e.g., on a display device), based on the triggering, the indication of the plurality of predefined spatial relationships and the indication of the spatial relationship between the surgical instrument and the through-hole.

The method of the first aspect may be performed by a processor. The method may be a computer-implemented method. The computer-implemented method may not comprise any surgical step. In particular, the computer-implemented method may not comprise any substantial physical interventions on a patient's body which require professional medical expertise to be carried out and which entail a substantial health risk even when carried out with the required professional care and expertise.

According to a second aspect, a processor is provided. The processor is configured to obtain implant data representative of a predetermined spatial relationship between an optical tracking pattern and a through-hole extending through an implant, obtain image data representative of at least a part of the optical tracking pattern, the image data having been acquired by an imaging unit attached to a surgical instrument, and obtain instrument data representative of a spatial relationship between the surgical instrument and the imaging unit at a point in time when the image data have been acquired. The processor is further configured to determine, based on the implant data, the image data and the instrument data, tracking data describing a spatial relationship between the surgical instrument and the through-hole, and obtain guidance data describing a plurality of predefined spatial relationships between the surgical instrument and the through-hole. The processor is further configured to trigger, based on the tracking data and the guidance data, simultaneous display of an indication of the plurality of predefined spatial relationships and an indication of the spatial relationship between the surgical instrument and the through-hole.

The processor may be configured to perform the method of the first aspect. The processor may be connected to a display device configured to simultaneously display, based on the triggering, the indication of the plurality of predefined spatial relationships and the indication of the spatial relationship between the surgical instrument and the through-hole.

According to a third aspect, a computer program is provided. The computer program comprises instructions which, when the program is executed by a processor (e.g., the processor of the second aspect), cause the processor to carry out the method of the first aspect.

According to a fourth aspect, a carrier is provided. The carrier contains the computer program of the third aspect. In other words, the carrier contains a computer program comprising instructions which, when the program is executed by a processor, cause the processor to: obtain implant data representative of a predetermined spatial relationship between an optical tracking pattern and a through-hole extending through an implant; obtain image data representative of at least a part of the optical tracking pattern, the image data having been acquired by an imaging unit attached to a surgical instrument; obtain instrument data representative of a spatial relationship between the surgical instrument and the imaging unit at a point in time when the image data have been acquired; determine, based on the implant data, the image data and the instrument data, tracking data describing a spatial relationship between the surgical instrument and the through-hole; obtain guidance data describing a plurality of predefined spatial relationships between the surgical instrument and the through-hole; and trigger, based on the tracking data and the guidance data, simultaneous display of an indication of the plurality of predefined spatial relationships and an indication of the spatial relationship between the surgical instrument and the through-hole. The carrier may be an electronic signal, an optical signal, a radio signal, or a (e.g., non-transitory) computer readable storage medium. The carrier may be a memory comprised in an apparatus, the apparatus further comprising the processor of the second aspect.

A surgical system may be provided comprising at least the processor of the second aspect and one or more of the surgical instrument, the optical tracking pattern, the imaging unit and the implant described herein. The surgical system may further comprise one or more of attachment members (as detailed below) and a tracking system configured to track a pose of at least one of the patient's body, the surgical instrument and the optical tracking pattern. The surgical system may further comprise a display device. The display device may be configured to simultaneously display, based on the triggering described with reference to the first aspect, the indication of the plurality of predefined spatial relationships and the indication of the spatial relationship between the surgical instrument and the through-hole.

BRIEF DESCRIPTION OF THE DRAWINGS

Further details, advantages and aspects of the present disclosure will become apparent from the following embodiments taken in conjunction with the drawings, wherein.

DETAILED DESCRIPTION

Figure 1:
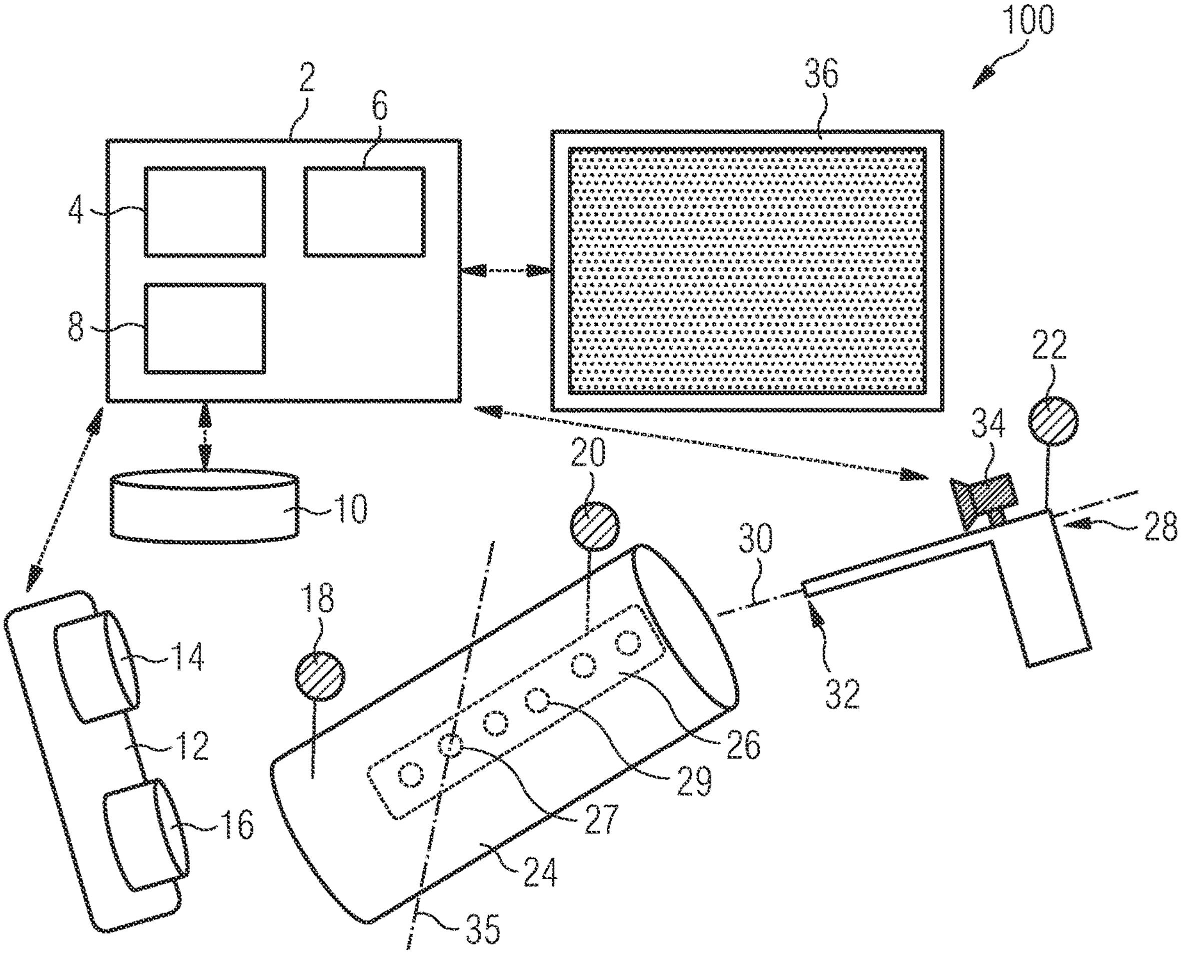
FIG. 1 schematically shows an exemplary embodiment of a surgical system in accordance with the present disclosure.

In the following description, exemplary embodiments of a surgical navigation system, a surgical navigation method and a visualization technique will be explained with reference to the drawings. The same reference numerals will be used to denote the same or similar structural features.

FIG. 1 schematically shows an exemplary embodiment of surgical system 100 in accordance with the present disclosure. The surgical system 100 comprises an apparatus 2 comprising a processor 4, a memory 6 and an interface 8. The apparatus 2 may be connected (e.g., by a wireless or a wired connection) to a database 10. The processor 4 may obtain data from the memory 6 and the database 10. The apparatus 2 may be configured as a computer terminal located, for example, on a medical cart.

In the shown example, the apparatus 2 is connected to a stereo-camera 12, which may be part of a surgical tracking system. The stereo-camera 12 comprises two sensor units 14, 16. The tracking system may, using the stereo-camera 12, be configured to track poses of trackers 18, 20 and 22. The trackers 18, 20 and 22 may each be a passive or an active optical marker. A passive optical marker may be realized by an arrangement of one or more reflective elements or by a graphical pattern, and an active optical marker may be realized by an arrangement of one or more light emitting diodes (LED). Note that one or more of the trackers 18, 20 and 22 may be of a different type than the other of the trackers 18, 20 and 22.

The tracker 20 may be removably coupled to or relative to an implant 26 (only indicated by dashed lines in FIG. 1). The tracker 20 may be removably attached to or relative to the implant 26 by one or more attachment members such as one or more attachment arms. The tracker 20, and, optionally, the one or more attachment members, may form a placement instrument. The placement instrument may be configured to enable a movement of the implant 26 into a desired pose by manually moving the placement instrument. The placement instrument, for example the one or more attachment members, may form or comprise a handle.

The tracker 20 comprises or consists of an optical tracking pattern. The optical tracking pattern of the tracker 20 may be provided or disposed on, or attached to, a flat surface of the tracker 20. The optical tracking pattern of the tracker 20 may comprise or consist of a two-dimensional or three-dimensional pattern. The optical tracking pattern of the tracker 20 is configured to be detected or localized in an image comprising at least a part of the optical tracking pattern. The optical tracking pattern of the tracker 20 may comprise or consist of a graphical code pattern such as a one-dimensional (e.g., bar-) code or a two-dimensional (e.g., quick response, QR) code. In some variants, the optical tracking pattern does not encode (e.g., comprise or describe) information about the implant 26 (e.g., a dimension and location of the through-hole, a type or geometry of the implant 26, or the like). The optical tracking pattern may not encode any predetermined information. The optical tracking pattern may in particular not encode a spatial relationship between the optical tracking pattern of the tracker 20 relative to (e.g., a portion of) another component of the surgical system 100, such as the implant 26 or a through-hole extending through the implant 26.

Like the tracker 20, also the trackers 18 and 22 may be active optical markers or passive (e.g., reflective) markers such as passive marker spheres. The tracker 18 is attached in a fixed spatial relationship relative to a patient's body 24, for example a leg or the spine of the patient. The tracker 20 is attached in a fixed spatial relationship relative to the implant 26 (shown only in dashed lines in FIG. 1). The tracking system may be configured to track only the trackers 18 and 22. The tracking system may alternatively be configured to track all of the trackers 18, 20 and 22.

The implant 26 shown in dashed lines in FIG. 1 may be embedded within the patient's body. The implant 26 may be positioned underneath a surface of the patient's body 24. In other words, the implant 26 may be configured to be implanted into the body 24 of the patient such that it is not visible from an outside of the body 24 after implantation. In the following, a bone plate 26 is described as an example of the implant. Alternative variants of the implant are possible, for example a bone nail or an artificial organ. The features of the bone plate 26 described herein also apply to such variants.

In the example shown in FIG. 1, the tracker 20 is attached in a fixed spatial relationship relative to the bone plate 26. The bone plate 26 comprises at least one through-hole 27, 29 extending through the bone plate 26. The at least one through-hole 27, 29 may be configured as a fixation hole for fixing the bone plate 26 relative to the body 24, for example relative to a bone of the patient's body 24. The bone plate 26 may comprise a plurality of (e.g., non-parallel) through holes 27, 29. The surfaces or centers of the through-holes 27 and 29 may lie in different planes, the planes being orthogonal to the central axis of the respective through-hole 27 or 29. The bone plate 26 may be configured for minimal invasive surgery.

The tracker 22 is attached in a fixed spatial relationship relative to a surgical instrument 28. The instrument 28 may be a chisel, a drill, a bur, a trocar, a screwdriver, a pointer or the like. The instrument 28 has a longitudinal axis 30 and a distal tip 32. The surgical instrument 28 may be referred to as surgical tool. The surgical instrument 28 is configured to be inserted into the patient's body 24 by a surgeon during surgery.

An imaging unit 34, e.g., comprising or consisting of a camera, is attached in a fixed spatial relationship (e.g., rigidly) to the surgical instrument 28, preferably in a removable manner. The imaging unit 34 may be attached to the surgical instrument 28 via one or more connecting means such as a coupling. The imaging unit 34 is configured to acquire an image containing at least a part of the optical tracking pattern of the tracker 20. The imaging unit 34 may be configured to acquire a plurality of images and only provide the images as image data which contain at least a part of the optical tracking pattern of the tracker 20. The tracker 20 may be arranged externally to the patient's body 24, even if the implant (e.g., the bone plate 26) lies underneath the surface of or is embedded in the patient's body 24, as illustrated in FIG. 1. This configuration may enable surgical navigation even in case of minimal invasive surgery. In particular, this may enable localizing the optical tracking pattern of the tracker 20 in an image acquired by the imaging unit 34 to determine a relative pose between the implant and the imaging unit 34.

For example, the imaging unit 34 may be removably coupled to the surgical instrument 28 in a predetermined fixed relationship. The imaging unit 34 is communicatively connected to the apparatus 2 via a wireless or a wired connection. By attaching the imaging unit 34 relative to the surgical instrument 28, a compact surgical setup may be provided. Still further, using the localization of the optical pattern in the image acquired by the imaging unit 34, the need for additional tracking systems apart from the imaging unit 34 described herein may be avoided. In other words, the imaging unit 34 may be used as a tracking unit of a tracking system.

By tracking poses of the trackers 18 and 20 by the tracking system (e.g., using the camera 12 or the imaging unit 34), a relative spatial relationship between the surgical instrument 28 and the patient's body 24 can be determined. Note that a relative spatial relationship between the surgical instrument 28 and the patient's body 24 may be determined by localizing the tracker 18 in the image acquired by the imaging unit 34. By tracking poses of the trackers 18 and 20 by the tracking system, or by localizing the trackers 18 and 20 in one or more images acquired by the imaging unit 34, a relative spatial relationship between the implant and the patient's body 24 can be determined. For instance, a relative spatial relationship between the longitudinal axis 30 of the surgical instrument 28 and a central axis 35 of the through-hole 27 of the bone plate 26 can be determined based on at least one of the tracking and localizing.

In case patient image data, for example computed tomography (CT) or magnetic resonance (MR) image data of the patient's body 24, has been obtained and registered relative to the tracker 18, a pose of the surgical instrument 28 may be determined in coordinates of or relative to the patient image data.

The apparatus 2 is connected to a display 36 (e.g., via the interface 8), and may trigger output of certain indications and visualizations on the display 36. For example, the processor 4 of the apparatus 2 may trigger output of an indication of the determined pose of the surgical instrument 28 relative to the patient image data on the display 36.

Figure 2:
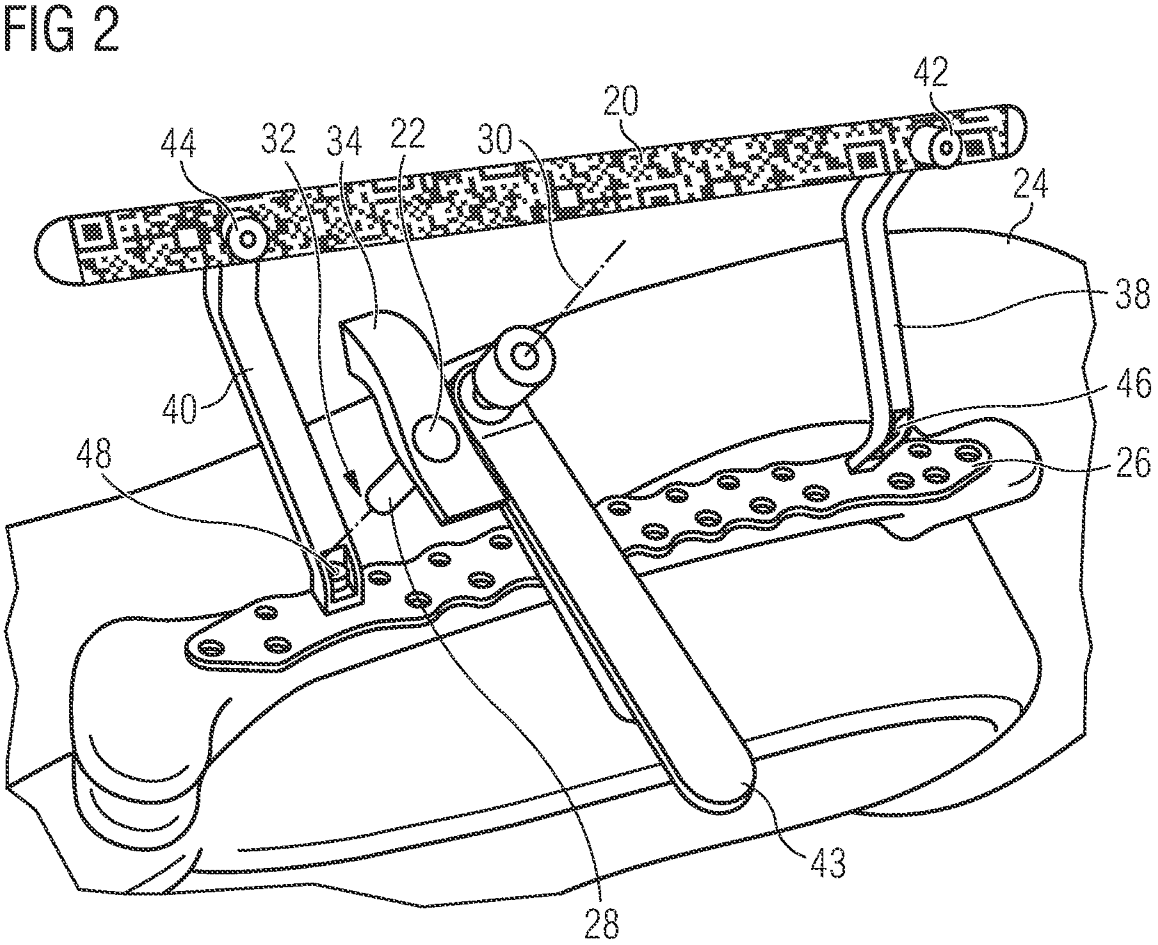
FIG. 2 shows first examples of parts of the exemplary embodiment of the surgical system of FIG. 1.

FIG. 2 shows first examples of parts of the surgical system 100. As can be seen, the tracker 20 has an elongated, bar-like shape. The tracker 20 in this example comprises a flat (e.g., essentially planar) surface. An graphical tracking pattern of the tracker 20 has been provided on the flat surface (e.g., has been etched into, painted, sprayed or glued onto the flat surface).

In the shown arrangement, the tracker 20 is coupled to the bone plate 26 via two arms 38, 40. The tracker may be removably attached to each of the arms 38, 40. Each of the arms 38, 40 is removably attached to the bone plate 26. For example, the tracker 20 is fixed to each of the arms 38, 40 by respective screws 42, 44. Each of the arms 38, 40 may be attached to the bone plate by respective screws 46, 48. At least one of the optical pattern of the tracker 20 and the essentially planar surface of the tracker 20 may be arranged essentially parallel or essentially orthogonal to the bone plate 26, depending on the relative pose between the imaging unit 34 and the surgical instrument 28. At least one of the optical pattern and the essentially planar surface may be arranged essentially orthogonal to a central axis of a through-hole of the implant (e.g., the central axis 35 of the through-hole 27 of the bone plate 26). This may ensure visibility of the optical tracking pattern of the tracker 20 for the imaging unit 34.

As can be seen, the tracker 22 may be part of or attached to the imaging unit 34. The imaging unit 34 and, optionally, the tracker 22, may be formed as a disposable device for single use. A field of view of the imaging unit 34 may comprise at least a part of the surgical instrument 28, for example, the distal tip 32. The imaging unit 34 may be arranged such that a (e.g., central) viewing axis of the imaging unit 34 lies essentially parallel to the longitudinal axis 30 of the surgical instrument 28. In the shown example, the surgical instrument 28 is a soft tissue sleeve attached to a handle 43 (e.g., for use as a surgical drill guide). Note that the handle 43 may be part of the surgical instrument 28 or removably coupled to the surgical instrument 28.

Figure 3:
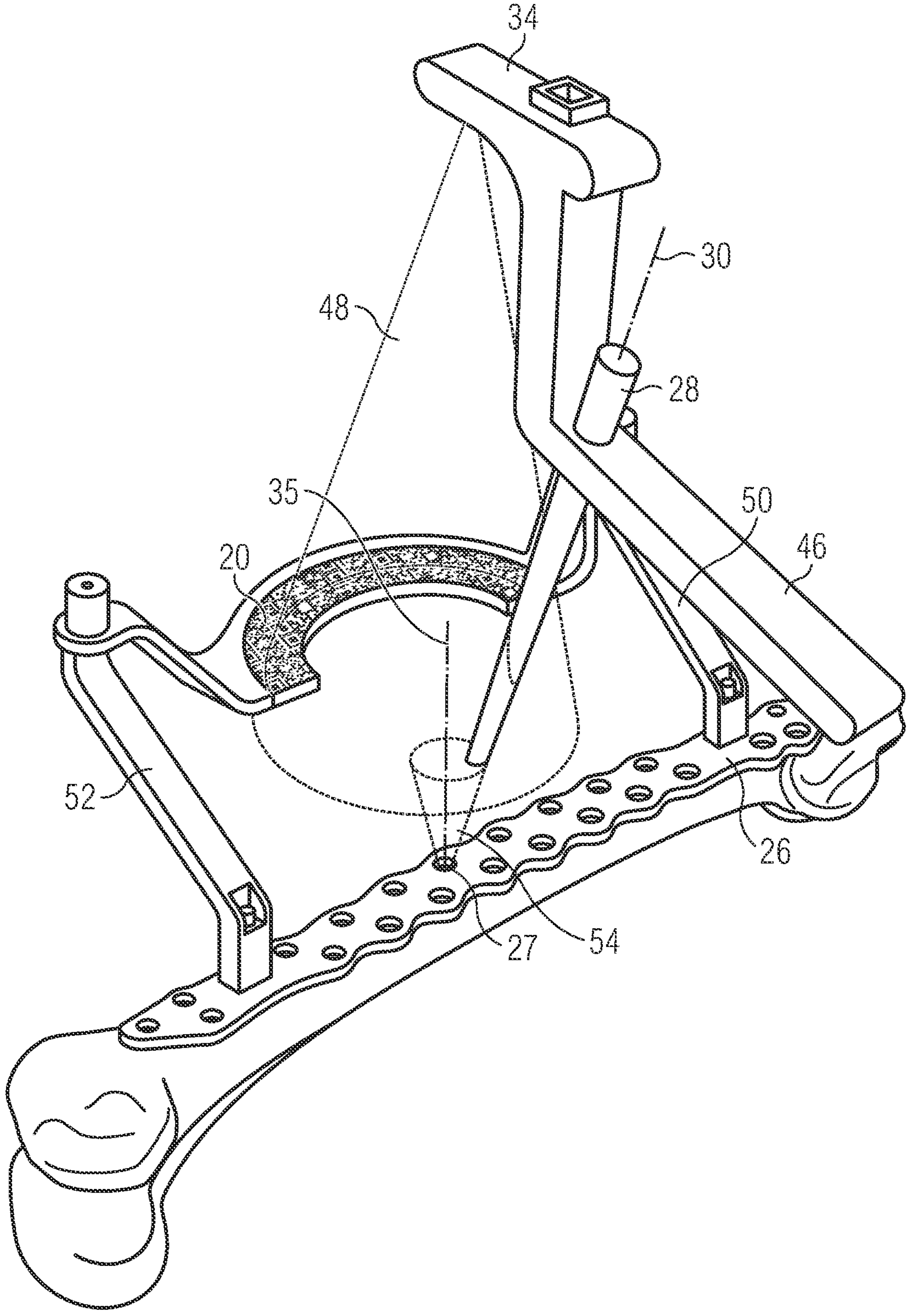
FIG. 3 shows second examples of parts of the exemplary embodiment of the surgical system of FIG. 1.

FIG. 3 shows second examples of parts of the surgical system 100. In this case, the imaging unit 34 is part of a housing forming a handle 47, the surgical instrument 28, in this exemplary case a trocar, being (e.g., removably) attached to the housing. A field of view 48 of the imaging unit 34 covers a front portion of the surgical instrument 28 including the distal tip 32. In addition, in the shown configuration, the field of view 48 of the imaging unit 34 comprises or covers at least a part of a graphical tracking pattern of the tracker 20. Similar to the example shown in FIG. 2, the tracker 20 is removably connected via a set of arms 50, 52 to the bone plate 26. The central axis 35 of through-hole 27 of the bone plate 26 is also shown in FIG. 3. As can be seen, the longitudinal axis 30 of the surgical instrument 28 is in the given pose of the surgical instrument 28 relative to the bone plate 26 not parallel to the central axis 35 of the through-hole 27.

FIG. 3 also schematically illustrates a cone 54, which defines a virtual border between a first region (inside the cone) and a second region (outside the cone). It will be appreciated that the virtual border could also be defined by other geometric bodies, such as a cylinder.

The cone 54 illustrated in FIG. 3 has a tip and a linearly tapered form. The first region may be referred to as a first volume and the second region may be referred to as a second volume. The border is determined such that, when the surgical instrument 28 is in any one of a plurality of predefined (e.g., preferred) spatial relationships relative to the through-hole 27, it is positioned or oriented in the first region and, when it is in another spatial relationship not corresponding to one of the plurality of predefined spatial relationships, it is positioned or oriented in the second region. At least the first region may be a region in an operating space in which the surgical instrument 28 is capable of being positioned.

The surgical instrument 28 may be positioned in a region if a point on the longitudinal axis 30 of the surgical instrument 28, for example the distal tip 32 of the surgical instrument 28, lies within (i.e., inside of) the region. The surgical instrument 28 may be oriented in a region if a line coinciding with the longitudinal axis 30 of the surgical instrument 28 lies (e.g., completely or only) within the region or does not intersect the border. This may allow a fast and easy determination or definition of preferred poses of the surgical instrument 28 in three spatial dimensions.

In the example shown in FIG. 3, the first region is essentially rotationally symmetric around a center axis 35 of the through-hole 27. The first region is essentially conical and a tip of the first region (corresponding to the tip of the cone 54) lies on a center axis 35 of the through-hole 27. This location is be advantageous in case of the through-hole 27 being configured to fix the bone plate 26 to the patient's body 24 using a poly-axial fixation screw (or any other bone fixation member) capable of being inserted in the through-hole 27 in a range of angles. In other words, the cone 54 may define advantageous poses of the surgical instrument 28 relative to the through-hole 27.

For example, a screw may be capable of being inserted into the through-hole at an angle within an angular range defined by a geometry of at least one of the through-hole 27 and the bone plate 26. This angular range may define the opening angle of the cone 54. The geometry (e.g., at least one of shape and size) of the first region may depend on a type of the implant, geometrical properties of the implant, a type of the through-hole 27 (e.g., for mono-axial screws or for poly-axial screws), a type of the surgical instrument 28 (e.g., a trocar or a screwdriver to screw screws through the through-hole 27 and into the bone), and anatomical properties of the patient's body (e.g., poses of critical anatomical elements, poses of bones, poses of organs, or the like) for example derived from the patient image data.

Figure 4:
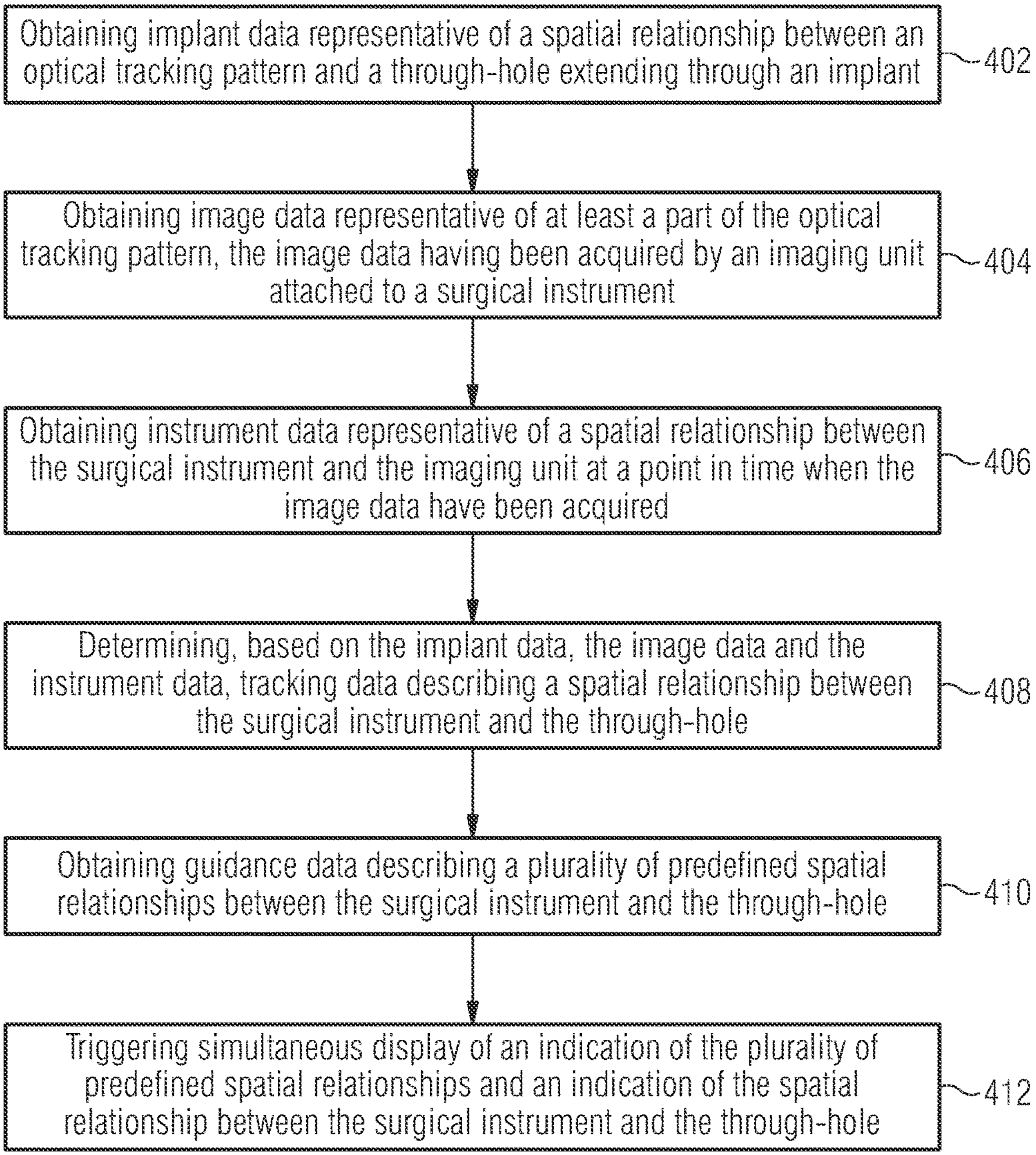
FIG. 4 shows a flow diagram of an exemplary method embodiment in accordance with the present disclosure.

FIG. 4 shows a flow diagram of an exemplary method embodiment in accordance with the present disclosure. The method may be performed by a processor, such as the processor 4 shown in FIG. 1. In the following, the method will be described with reference to FIGS. 1 to 3, although the method may equally apply to other variants of the components (e.g., the bone plate 26, the imaging unit 34, the tracker 20 etc.) described with reference to these drawings.

In a step 402, the implant data is obtained. The implant data comprises, describes or is representative of a (e.g., predetermined, fixed, known or stationary) spatial relationship between an optical tracking pattern (e.g., the optical tracking pattern of the tracker 20) and a through-hole (e.g., the through-hole 27) extending through an implant (e.g., the bone plate 26). This spatial relationship may comprise or consist of a pose (i.e., at least one of a position and an orientation) of the optical tracking pattern of the tracker 20 relative to the through-hole 27.

The implant data may be obtained (e.g., received or retrieved by the processor 4) from the memory 6 or from the database 10. The implant data is in one variant not encoded in the optical tracking pattern of the tracker 20. This approach may enable using different implants with the same optical tracking pattern, thereby saving costs in surgical procedures. In addition, this approach may avoid having to extract information from the pattern, thereby saving computing resources and time. Still further, this approach may avoid incorrect information being extracted from low quality images of the optical tracking pattern, for example images comprising only small portions (e.g., less than 10%) of the optical tracking pattern of the tracker 20.

In a step 404, image data is obtained. The image data is representative of at least a part of the optical tracking pattern (e.g., the optical tracking pattern of the tracker 20). For example, the image data may comprise or consist of an image of the at least a part of the optical tracking pattern of the tracker 20. The image data may comprise at least one or exactly one image representative of (e.g., containing, depicting or describing) the at least a part of the optical tracking pattern of the tracker 20. The image data has been acquired by an imaging unit (e.g., the imaging unit 34) attached (e.g., stationarily or in a fixed pose relative) to a surgical instrument (e.g., the surgical instrument 28).

The step of acquiring the image (e.g., by the imaging unit 34) in one example may not be part of the method described herein. The image data may be obtained from the memory 6 or from the database 10. The step 402 may be performed after, simultaneously with, or before the step 404. For example, the implant data may be obtained before any image is acquired by the imaging unit 34.

In a step 406, instrument data is obtained. The instrument data is representative of a (e.g., predetermined, known, fixed or stationary) spatial relationship between the surgical instrument (e.g., the surgical instrument 28) and the imaging unit (e.g., the imaging unit 34) at a point in time when the image data have been acquired, for example by describing, comprising or consisting of a relative pose between the surgical instrument 28 and the imaging unit 34 at the point in time.

The instrument data may be obtained from the memory 6 or from the database 10. The step 406 may be performed after, simultaneously with, or before any of the steps 402 and 404.

In a further step 408, based on the implant data, the image data and the instrument data, tracking data is determined. The tracking data describes a spatial relationship (e.g., a relative pose) between the surgical instrument (e.g., the surgical instrument 28) and the through-hole (e.g., the through-hole 27). For example, based on the image data, a spatial relationship between the imaging unit 34 and the optical tracking pattern of the tracker 20 may be determined by localizing at least a part of the optical tracking pattern of the tracker 20 in an image of the image data.

The method may comprise determining the tracking data by calculating an aggregate transformation or a chain of transformations as the spatial relationship between the surgical instrument 28 and the through-hole 27. The aggregate transformation may be determined as a sum of the spatial relationship between the surgical instrument 28 and the imaging unit 34, the spatial relationship between the imaging unit 34 and the optical tracking pattern of the tracker 20, and the spatial relationship between the optical tracking pattern of the tracker 20 and the through-hole 27 of the bone plate 26. This may enable reliably determining the relative pose between the surgical instrument 28 and the through-hole 27 using image data acquired by the imaging unit 34 (e.g., removably) attached to the surgical instrument 28.

In a step 410, guidance data is obtained. The guidance data describes a (e.g., the) plurality of predefined (e.g., preferred) spatial relationships between the surgical instrument (e.g., the surgical instrument 28) and the through-hole (e.g., the through-hole 27). The guidance data may pre-operatively be determined by a surgeon. Also, the guidance data may automatically be determined by the processor 4 or by a different processor. The guidance data may be obtained from the memory 6 or from the database 10. For example, the predefined spatial relationships may be determined based on at least one of (e.g., geometrical or material) properties of the implant, (e.g., geometrical or material) properties of the surgical instrument 28, a type of the surgical instrument 28 such as a trocar, a screwdriver or the like, and the patient image data.

As explained with reference to FIG. 3, the plurality of predefined spatial relationships between the surgical instrument 28 and the through-hole 27 may also be referred to as a plurality of preferred or advantageous spatial relationships. For example, the predefined spatial relationships may avoid harm of (e.g., critical) anatomical structures of the patient's body 24 by the surgical instrument 28. The predefined spatial relationships may enable a reliable fixation of the bone plate 26 to the body 24 using fixation screws when the surgical instrument 28 is used to place the fixation screws. The predefined spatial relationships may be defined as a continuous range or volume of such relationships.

In a step 412, based on the tracking data and the guidance data, simultaneous display of an indication of the plurality of predefined (e.g., preferred) spatial relationships and an indication of the spatial relationship between the surgical instrument (e.g., the surgical instrument 28) and the through-hole (e.g., the through-hole 27) is triggered. For example, the indications are triggered by the processor 4 to be simultaneously displayed (e.g., in a same rendered image) on the display 36. The step of triggering, based on the tracking data and the guidance data, the simultaneous display means that both the indication of the plurality of predefined spatial relationships and the indication of the spatial relationship between the surgical instrument 28 and the through-hole 27 are triggered to be displayed simultaneously (i.e., at the same time). The simultaneous display may comprise displaying the respective indications on a same display, for example in a same rendered image. The simultaneous display may comprise displaying the respective indications in an overlaid or overlapped manner with one another. For example, a trigger signal may be transmitted to the display 36 to configure the display 36 to simultaneously display both the indication of the plurality of predefined spatial relationships and the indication of the spatial relationship between the surgical instrument 28 and the through-hole 27.

Accordingly, an image acquired by the imaging unit 34 attached to the surgical instrument 28 is used to determine the spatial relationship between the surgical instrument 28 and the through-hole 27. This approach may provide a reliable determination of the spatial relationship, as a visibility of the optical tracking pattern of the tracker 20 to the imaging unit 34 may be ensured for many relative poses between the surgical instrument 28 and the bone plate 26, in particular for the predefined or preferred spatial relationships between the surgical instrument 28 and the bone plate 26. By triggering simultaneous display of the indication of the plurality of (e.g., preferred) predefined spatial relationships and of the indication of the spatial relationship between the surgical instrument 28 and the through-hole 27, surgical navigation may be improved. For example, not only a momentary relative pose between the surgical instrument 28 and the through-hole 27 is provided, but also a comparison thereof with the (e.g., preferred) predefined spatial relationships is possible. A surgeon may thus change a pose of the surgical instrument 28 advantageously to correspond or match with the (e.g., preferred) predefined spatial relationships, yielding improved surgical results.

The provision of the plurality of (e.g., preferred) predefined spatial relationships instead of just one predefined spatial relationship may enable a surgeon to choose which predefined relationship best suits the surgical task at hand (e.g., inserting a mono-axial or a poly-axial fixation screw into the through-hole 27). Therefore, surgical navigation may be improved, which may also yield improved surgical results.

The method may further comprise a step of selecting one of a plurality of through-holes comprised in the implant, for example selecting the through-hole 27 of the through-holes 27 and 29 of the bone plate 26 (not illustrated in FIG. 4). The selection may be based on a spatial relationship between the surgical instrument 28 and the through-hole 27 or based on the tracking data. For example, a through-hole, which is closest to the longitudinal axis 30 of the surgical instrument 28, may be selected. The selected through-hole may then be used as the through-hole in (e.g., a further execution of) steps 402, 408, 410 and 412.

Note that the indication of the plurality of predefined (e.g., preferred) spatial relationships and the indication of the spatial relationship between the surgical instrument 28 and the through-hole 27 may be used by the processor 4 to determine a surgical treatment plan. That is, the method may comprise a step of determining, based on the indication of the plurality of predefined (e.g., preferred) spatial relationships and the indication of the spatial relationship between the surgical instrument 28 and the through-hole 27, a treatment plan for use in surgical navigation (not illustrated in FIG. 4). The treatment plan may define at least one of an optimized trajectory of the surgical instrument 28 to the through-hole 27 and an optimized relative pose between the longitudinal axis 30 of the surgical instrument 28 and the central axis 35 of the through-hole 27. In one variant, the step of determining the treatment plan may be performed alternatively to the step of triggering simultaneous display. The treatment plan may provide guidance for a surgeon in surgical navigation, which may improve surgical results.

The indication of the plurality of predefined spatial relationships may comprise a visualization of at least a part of the border, for example a (e.g., perspective or three-dimensional) visualization of the cone 54 as shown in FIG. 3. The visualization may comprise or consist of a two-dimensional projection of the at least the part of the border into a viewing plane. This may enable a fast and reliable determination of how the surgical instrument 28 shall be moved relative to the bone plate 26, thereby improving surgical efficiency.

The indication of the plurality of predefined spatial relationships may comprise a different visualization of at least a part of the first region compared to the second region or a different visualization of at least a part of the second region compared to the first region. As an example, the visualizations may differ from one another by at least one representational property chosen from color, contrast, brightness, hue, saturation, optical pattern or the like. The visualizations may differ from one another by a time-dependent change of the at least one representational property (e.g., blinking, color change or pattern change). In other words, the first region may be highlighted with respect to the second region or vice versa. This may allow a fast differentiation between the preferred spatial relationships and other spatial relationships between the surgical instrument 28 and the through-hole 27.

At least one of the visualized part of the border and the part of the first or second region with a different visualization may lie within a predetermined maximal distance from a center or center axis 35 of the through-hole 27. The center may be a point on the center axis 35 of the through-hole and be positioned (e.g., in the middle) between an upper surface and a lower surface of the bone plate 26, wherein the through-hole extends between the upper surface and the lower surface. The center may be a point on the center axis 35 of the through-hole 27 and be positioned in a plane defined by the upper surface or the lower surface of the bone plate 26, wherein the through-hole 27 extends between the upper surface and the lower surface. The part of the first or second region may lie between a first plane in which the center of the through-hole 27 lies and which is parallel to at least one of the upper and the lower surface of the bone plate 26, and a second plane parallel to the first plane, wherein a distance between the first plane and the second plane corresponds to the predetermined maximal distance. This may be advantageous as surgical navigation is especially useful for positions of the distal tip 32 of the surgical instrument 28, which are in close proximity to the surgical target, e.g., the through-hole 27. This may also avoid determining or obtaining large amounts of spatial positions as falling into the first region or the second region, thereby decreasing the amount of required computing time and resources.

The indication of the spatial relationship between the surgical instrument 28 and the through-hole 27 may comprise a visualization of an orientation of the axis 30 of the surgical instrument 28 relative to the center axis 35 of the through-hole 27. Such a relative orientation is also indicated in FIG. 3. This may enable a fast determination of the indication triggered to be displayed. In addition, an advantageous relative pose between the through-hole 27 and the surgical instrument 28 can be provided in a fast manner, thereby enabling a precise and real-time surgical navigation.

The indication of the spatial relationship between the surgical instrument 28 and the through-hole 27 may, alternatively or additionally, comprise a visualization of an offset of the tip 32 of the surgical instrument 28 from the center axis 35 of the through-hole 27. The step 412 may comprise triggering display of a visualization representing a view along the axis 30 of the surgical instrument 28, the visualization further visualizing the at least a part of the border and, optionally, the center axis 35 of the through-hole 27. Alternatively or additionally, the step 412 may comprise triggering display of a visualization representing a view along the center axis 35 of the through-hole 27, the visualization further visualizing the at least a part of the border and, optionally, the axis 30 of the surgical instrument 28. This may provide views capable of being intuitively understood by a surgeon. That is, movement of the surgical instrument 28 in these cases may be directly represented in the visualization, which minimizes the coordinative capabilities a surgeon needs to employ when using the visualization for surgical navigation. In other words, these visualizations are tailored to the cognitive and coordinative capabilities of a human brain.

As noted above, patient image data may be registered relative to the tracker 20. That is, a transformation between a coordinate system of the patient image data and a coordinate system of the tracker 20 may be known or determined (e.g., using a commonly known surgical registration technique). In this case, a visualization of the patient data may be triggered to be displayed, preferably simultaneously with the indication of the plurality of predefined spatial relationships and the indication of the spatial relationship between the surgical instrument 28 and the through-hole 27. These indications may be displayed, e.g., overlaid on or superimposed onto the (e.g., rendering or visualization of the) patient image data.

Figure 5:
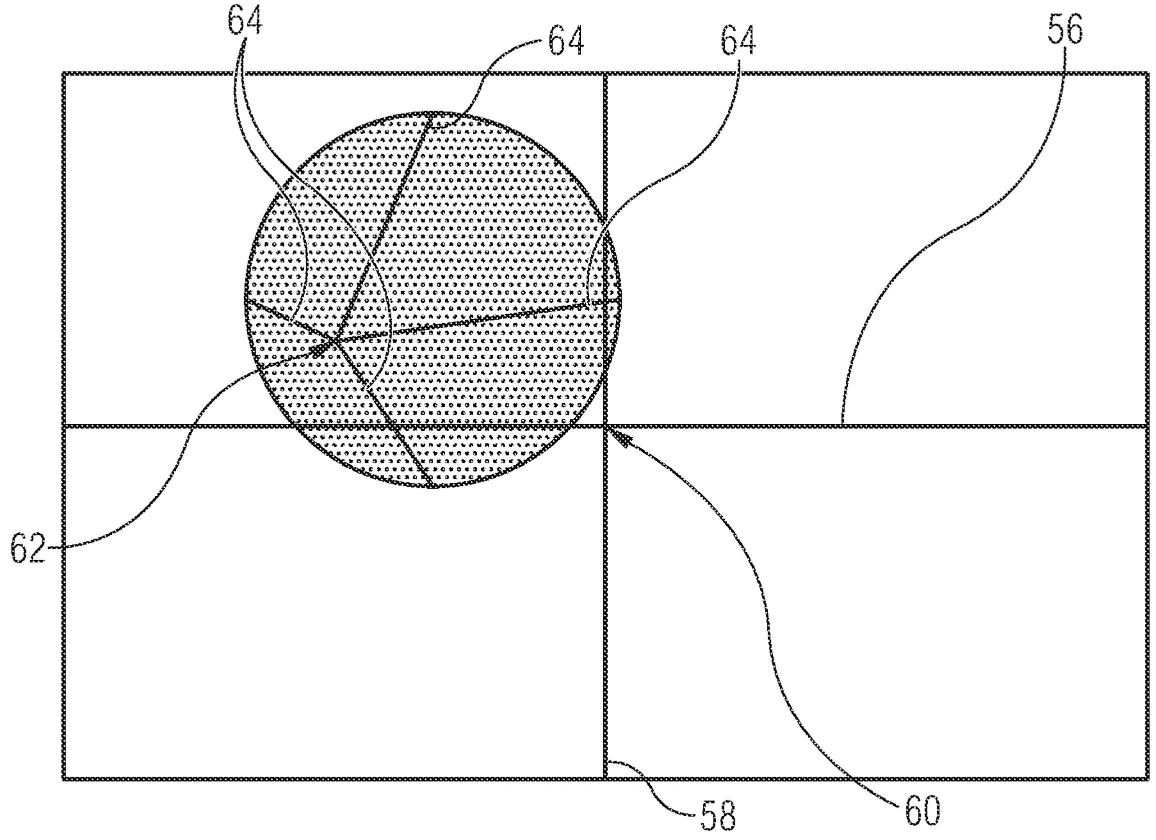
FIG. 5 shows an exemplary visualization in accordance with the present disclosure.

FIG. 5 shows an exemplary simultaneous display view by the display 36. As can be seen, a first pair of crosshairs 56, 58 may be displayed by the display 36. An intersection point 60 of the first pair of crosshairs 56, 58 in a first variant lies on the axis 30 of the surgical instrument 28. In this variant, the shown visualization represents a view along the axis 30. Also indicated is a two-dimensional projection of the cone 54 into a viewing plane orthogonal to the axis 30. A point 62 indicates the tip of the cone 54. A plurality of lines 64 further helps in understanding the orientation of the cone 54 relative to the axis 30. The lines 64 are straight lines on the surface of the cone 54 intersecting at the point 62 on the tip of the cone, which have been projected into the viewing plane.

In a second variant, the shown visualization represents a view along the center axis 35. The intersection point 60 of the first pair of crosshairs 56, 58 in this case lies on the center axis 35 of the through-hole 27. In the second variant, a two-dimensional projection of a cone into a viewing plane orthogonal to the center axis 35 is shown. The tip of the cone in this case is fixed relative to the distal tip 32 of the surgical instrument 28, wherein the cone represents the border described herein. The point 62 indicates the tip of this cone. The plurality of lines 64 further helps in understanding the orientation of the cone relative to the center axis 35. As in the first variant, the lines 64 are straight lines on the surface of the cone intersecting at the tip of the cone, which have been projected into the viewing plane.

As will be apparent from the above, the present disclosure provides an advantageous technique for surgical navigation. In particular, even if the implant is not visible to a tracking system placed remote from the patient, a relative position between the surgical instrument and the implant may be determined and provided to a surgeon for guidance.

Also, by using the imaging unit attached relative to the surgical instrument, a visibility of the optical tracking pattern may be ensured, at least once the surgical instrument is roughly aligned in an insertion direction.

Not only a relative pose between the surgical instrument, but also a plurality of preferred spatial relationships between the surgical instrument and the implant may be provided, thereby further improving the surgical navigation.

Visualizations of relative spatial positions are described herein, changes of which, caused by movements of the surgical instrument, are easy to understand and follow by a surgeon. A variety of visualizations has been described herein which minimize the cognitive and coordinative requirements for surgeons during surgical navigation and minimize the amount of required computer processing time and resources while providing an advantageous navigational accuracy and response time.

The invention claimed is:

1. A surgical navigation method comprising:

inserting an implant into a patient's body in a desired pose using a placement instrument comprising a two-dimensional optical tracking pattern, wherein the optical tracking pattern is disposed on, or attached to, a flat surface of the implant, the implant comprising a through-hole; and navigating a surgical instrument relative to the inserted implant, the surgical instrument having an imaging unit attached thereto, the navigating being performed using a displayed indication of a spatial relationship between the surgical instrument and the through-hole that is at least based on a localization of the optical tracking pattern in image data acquired by the imaging unit, the image data being representative of at least a part of the optical tracking pattern, wherein the optical tracking pattern does not encode information about the implant.

2. The method of claim 1, wherein the step of navigating the surgical instrument further comprises using a simultaneously displayed indication of a plurality of predefined spatial relationships between the surgical instrument and the through-hole.

3. The method of claim 2, wherein the step of navigating the surgical instrument further comprises changing a pose of the surgical instrument relative to the implant such that the pose of the surgical instrument matches one or more of the predefined spatial relationships.

4. The method of claim 2, wherein the plurality of predefined spatial relationships is defined by a border with respect to the through-hole, the border separating a first region in space from a second region in space.

5. The method of claim 4, wherein the border is defined such that, when the surgical instrument is in any one of the plurality of predefined spatial relationships, it is located in the first region and, when it is in another spatial relationship not corresponding to one of the plurality of predefined spatial relationships, it is located in the second region.

6. The method of claim 4, wherein a geometry of the first region depends on at least one of the following parameters:

a type of the implant;

geometrical properties of the implant;

a type of the through-hole;

a type of the surgical instrument;

anatomical properties of the patient's body.

7. The method of claim 4, wherein the simultaneously displayed indication of the plurality of predefined spatial relationships comprises a visualization of at least a part of the border.

8. The method of claim 7, wherein the step of navigating the surgical instrument further comprises using a displayed visualization representing a view along an axis of the surgical instrument, the visualization further visualizing the at least a part of the border.

9. The method of claim 7, wherein the step of navigating the surgical instrument further comprises using a displayed visualization representing a view along a center axis of the through-hole, the visualization further visualizing the at least a part of the border.

10. The method of claim 4, wherein the simultaneously displayed indication of the plurality of predefined spatial relationships comprises a different visualization of at least a part of the first region compared to the second region or a different visualization of at least a part of the second region compared to the first region.

11. The method of claim 4, wherein the first region is rotationally symmetric around a center axis of the through-hole.

12. The method of claim 2, further comprising pre-operatively defining the plurality of spatial relationships.

13. The method of claim 1, wherein the displayed indication of the spatial relationship between the surgical instrument and the through-hole comprises a visualization of a pose of an axis of the surgical instrument relative to a center axis of the through-hole.

14. The method of claim 1, wherein the displayed indication of the spatial relationship between the surgical instrument and the through-hole comprises a visualization of an offset of a tip of the surgical instrument from a center or center axis of the through-hole.

15. The method of claim 1, wherein the implant comprises a plurality of through-holes, the method further comprising selecting one of the plurality of through-holes as said through-hole.

16. The method of claim 1, further comprising inserting a screw through the through-hole using the surgical instrument.

17. The method of claim 16, further comprising screwing the screw into a bone of the patient's body to fix the implant onto the bone.

18. The method of claim 1, further comprising obtaining, before any image is acquired by the imaging unit, implant data, from a memory or a database, wherein the implant data is representative of a spatial relationship between the optical tracking pattern and the through-hole extending through the implant.

19. The method of claim 1, wherein the imaging unit is a camera.

* * * * *